(12) United States Patent
Jo et al.

(10) Patent No.: US 8,329,191 B2
(45) Date of Patent: Dec. 11, 2012

(54) THREE-BRANCHED POLYETHYLENE GLYCOL-G-CSF CONJUGATE

(75) Inventors: Yeong-Woo Jo, Seoul (KR); Won-Young Yoo, Seoul (KR); Hyun-Kyu Jeon, Yongin-si (KR); Yun-Kyu Choi, Seongnam-si (KR); Hye-In Jang, Seoul (KR); Byong-Moon Kim, Seoul (KR); Sung-Hee Lee, Seoul (KR); Soo-Hyung Kang, Yongin-si (KR); Moo-Hi Yoo, Seoul (KR)

(73) Assignee: Dong-A-Pharm. Co., Ltd., Seoul (KR)

( * ) Notice: Subject to any disclaimer, the term of this patent is extended or adjusted under 35 U.S.C. 154(b) by 167 days.

(21) Appl. No.: 12/515,122

(22) PCT Filed: Nov. 22, 2006

(86) PCT No.: PCT/KR2006/004908
§ 371 (c)(1),
(2), (4) Date: Jul. 22, 2009

(87) PCT Pub. No.: WO2008/060002
PCT Pub. Date: May 22, 2008

(65) Prior Publication Data
US 2010/0105616 A1 Apr. 29, 2010

(30) Foreign Application Priority Data
Nov. 17, 2006 (KR) .......................... 10-2006-0113721

(51) Int. Cl.
A61K 38/00 (2006.01)
C07K 14/00 (2006.01)
A61K 38/19 (2006.01)
C07K 1/00 (2006.01)

(52) U.S. Cl. ............... 424/198.1; 424/193.1; 424/194.1; 424/195.11; 530/402; 530/391.9; 514/7.6; 514/3.3

(58) Field of Classification Search .................. None
See application file for complete search history.

(56) References Cited

U.S. PATENT DOCUMENTS

| | | | |
|---|---|---|---|
| 5,824,784 A | 10/1998 | Kinstler et al. | |
| 5,951,974 A | 9/1999 | Gilbert et al. | |
| 7,144,978 B2 * | 12/2006 | Huang et al. | 528/425 |
| 2004/0030101 A1 | 2/2004 | Bailon et al. | |
| 2005/0033058 A1 | 2/2005 | Huang et al. | |
| 2005/0058620 A1 | 3/2005 | Nakamoto et al. | |

FOREIGN PATENT DOCUMENTS

| | | |
|---|---|---|
| EP | 1479711 A1 | 11/2004 |
| EP | 1564236 A1 | 8/2005 |
| EP | 1586334 A1 | 10/2005 |
| KR | 10-0248111 A | 3/2000 |
| KR | 10-0254097 B1 | 5/2000 |
| KR | 1020030076417 A | 9/2003 |
| KR | 1020040086930 A | 10/2004 |
| KR | 10-0507796 B1 | 8/2005 |
| KR | 10-508358 B1 | 8/2005 |
| WO | 9611953 A1 | 4/1996 |
| WO | 0044785 A1 | 8/2000 |
| WO | 2004/083242 A1 | 9/2004 |
| WO | 2005/055946 A2 | 6/2005 |
| WO | 2005099769 A2 | 10/2005 |
| WO | 2006024953 A2 | 3/2006 |

OTHER PUBLICATIONS

Y. Jo, et al.: "Pharmacokinetics and tissue distribution of rhG-CSF conjugated with different sizes of PEGs in SD rats," poster presented at 33rd Annual Meeting & Exposition of the controlled Release Society, Austria Center, Vienna, Austria, Jul. 22-26, 2006, 5 pages.
Korean Office Action issued in Korean Application No. 10-2006-0113721 dated Jun. 23, 2010, 5 pages.
Defrees et al., "GlycoPEGylation of recombinant therapeutic proteins produced in *Escherichia coli*", Glycobiology, vol. 16 No. 9, pp. 833-843, 2006.
Hill et al., "Allogeneic Stem Cell Transplantation with Peripheral Blood Stem Cells Mobilized by Pegylated G-CSF", Biology of Blood and Marrow Transplantation, 12: 603-607 (2006).
Satake-Ishikawa et al., "Chemical Modification of Recombinant Human Granulocyte Colony-Stimulating Factor by Polyethylene Glycol Increases its Biological Activity in vivo", Cell Structure and Function, 17: 157-160 (1992).

\* cited by examiner

*Primary Examiner* — Elly-Gerald Stoica
(74) *Attorney, Agent, or Firm* — Rothwell, Figg, Ernst & Manbeck, P.C.

(57) ABSTRACT

The present invention relates to three-branched PEG-G-CSF conjugate of general formula (1) in which the bonding ratio of three-branched polyethylene glycol (PEG) and G-CSF is 1:1 (mol/mol), wherein PEG has an average molecular weight of from 200 to 45,000 daltons; a pharmaceutical composition comprising the same, and a preparing method thereof.

8 Claims, 11 Drawing Sheets

[Fig. 1]
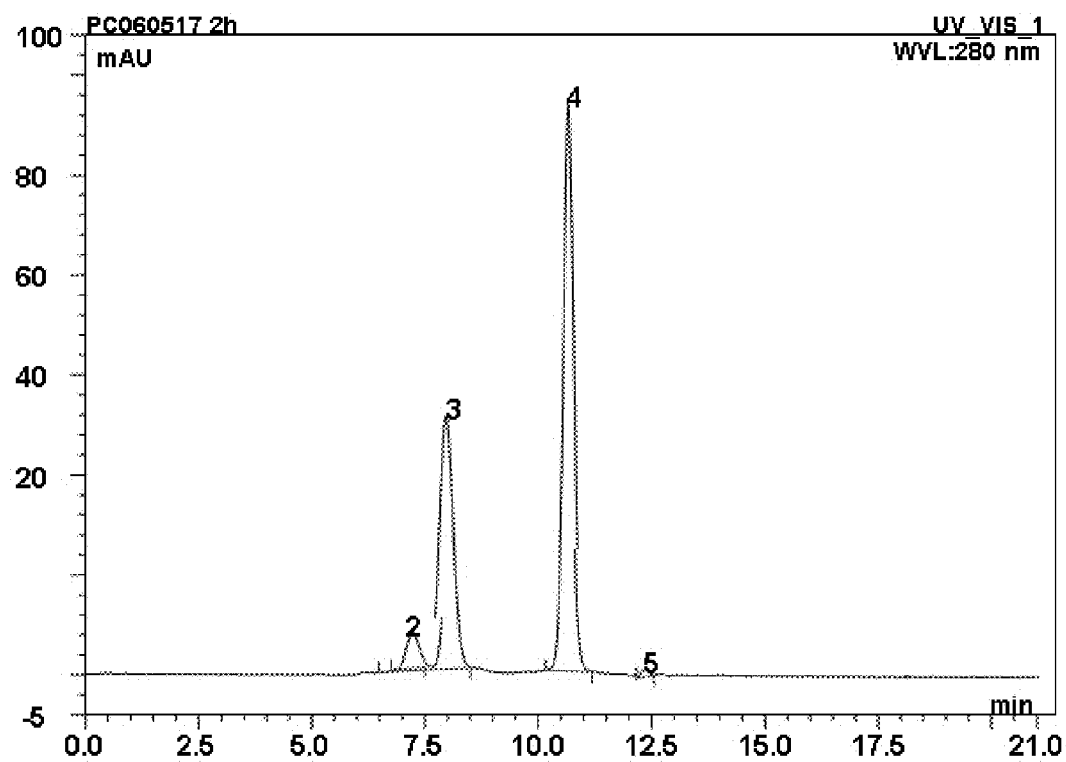

[Fig. 2]
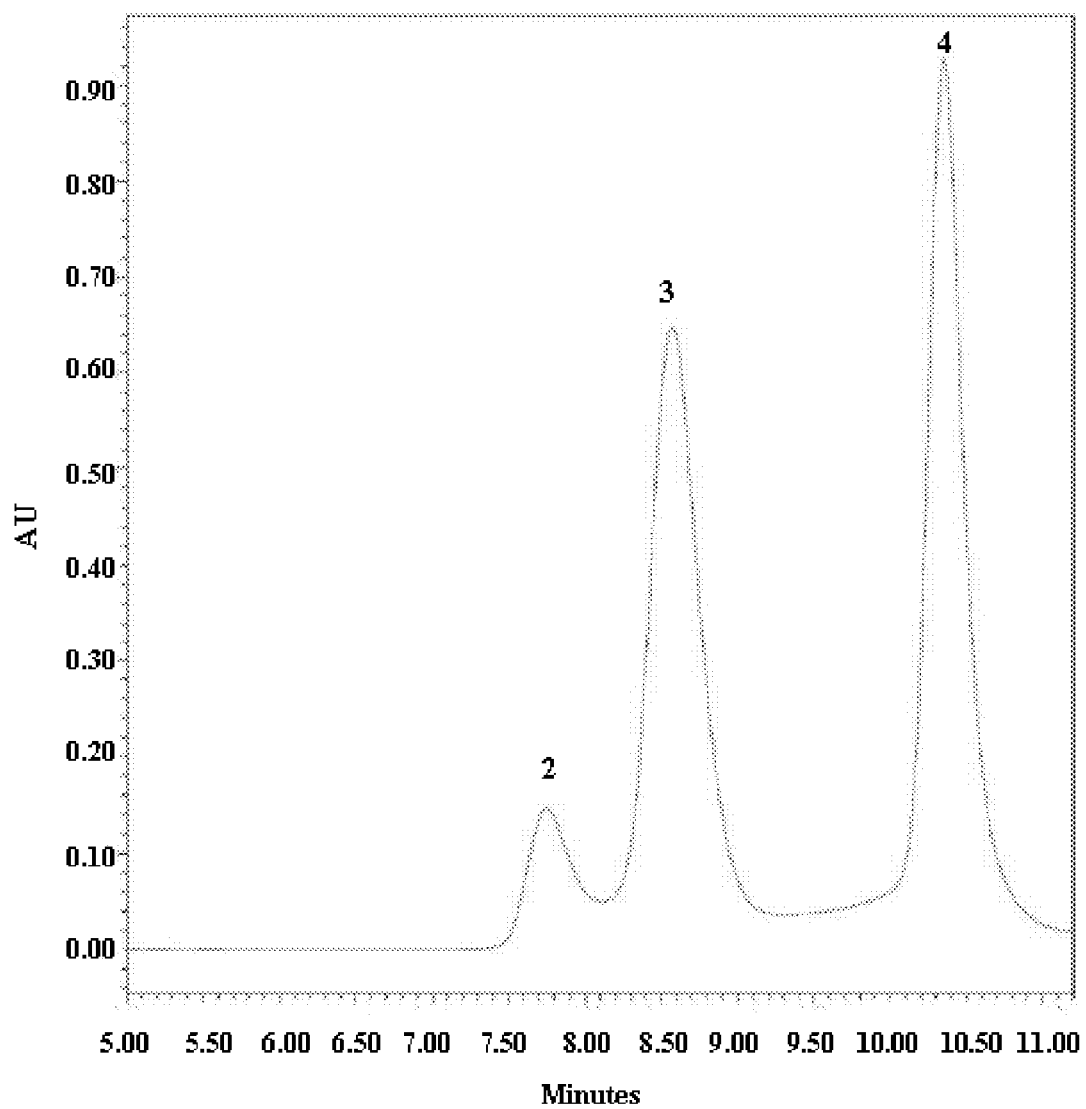

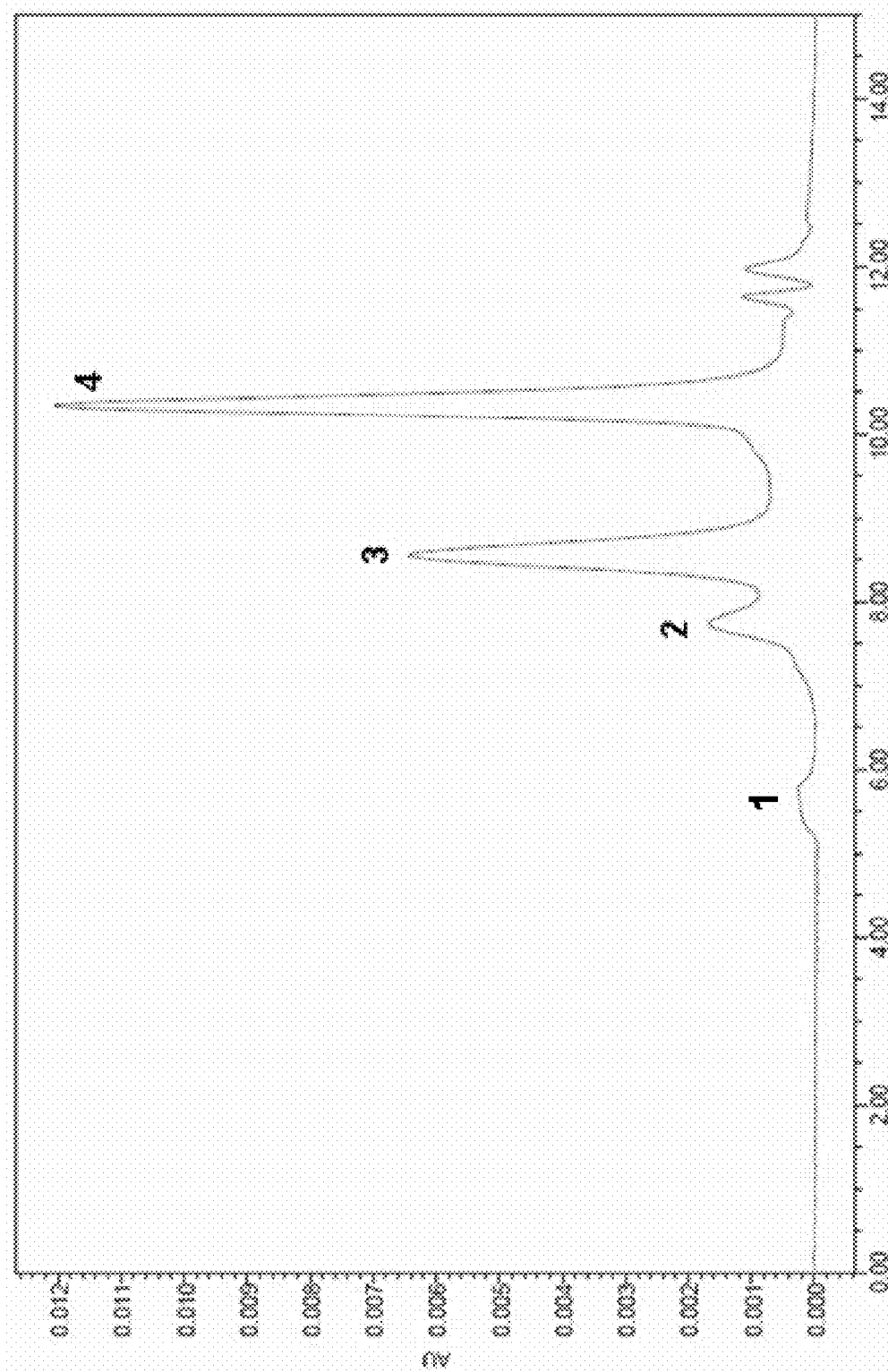

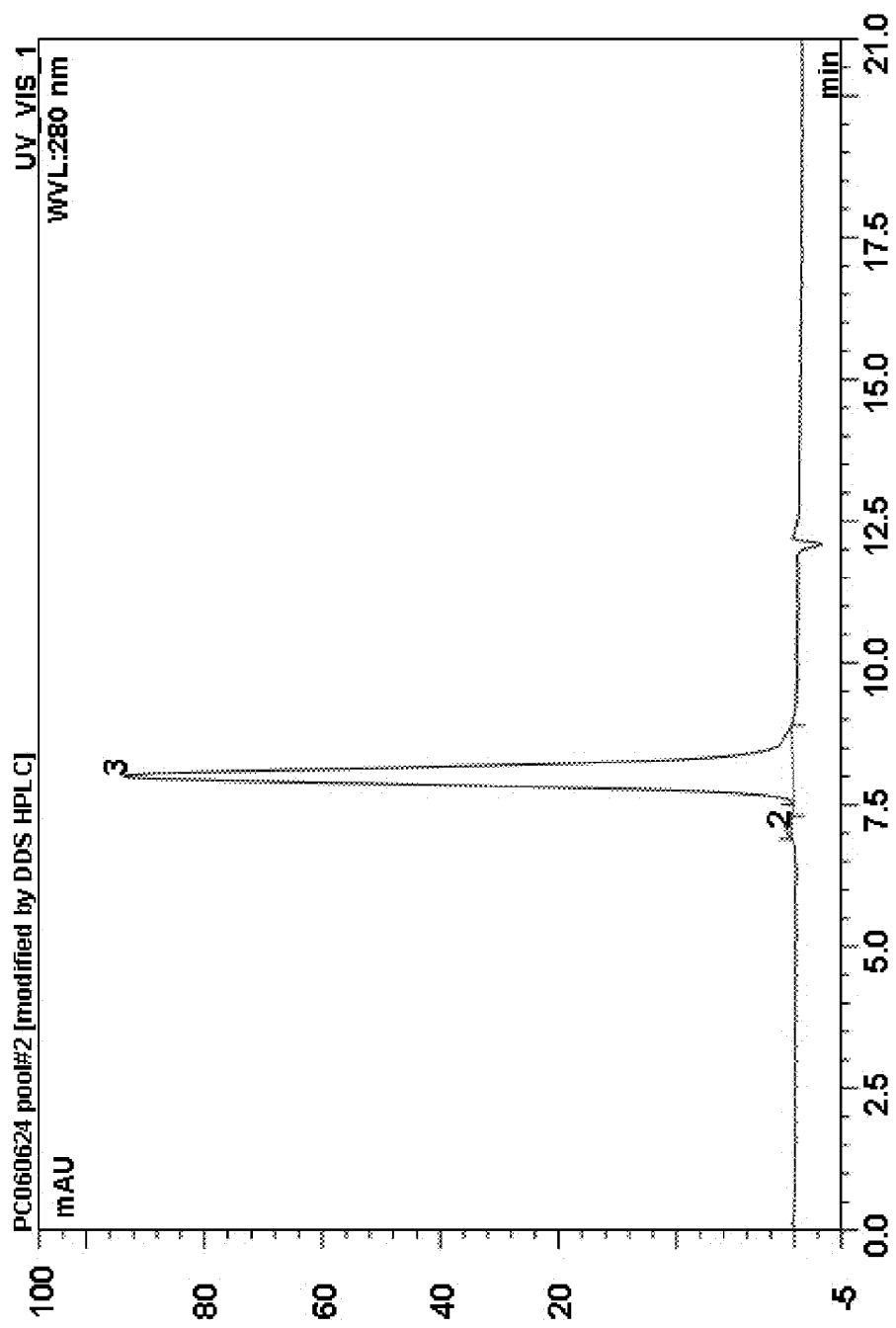

[Fig. 5]
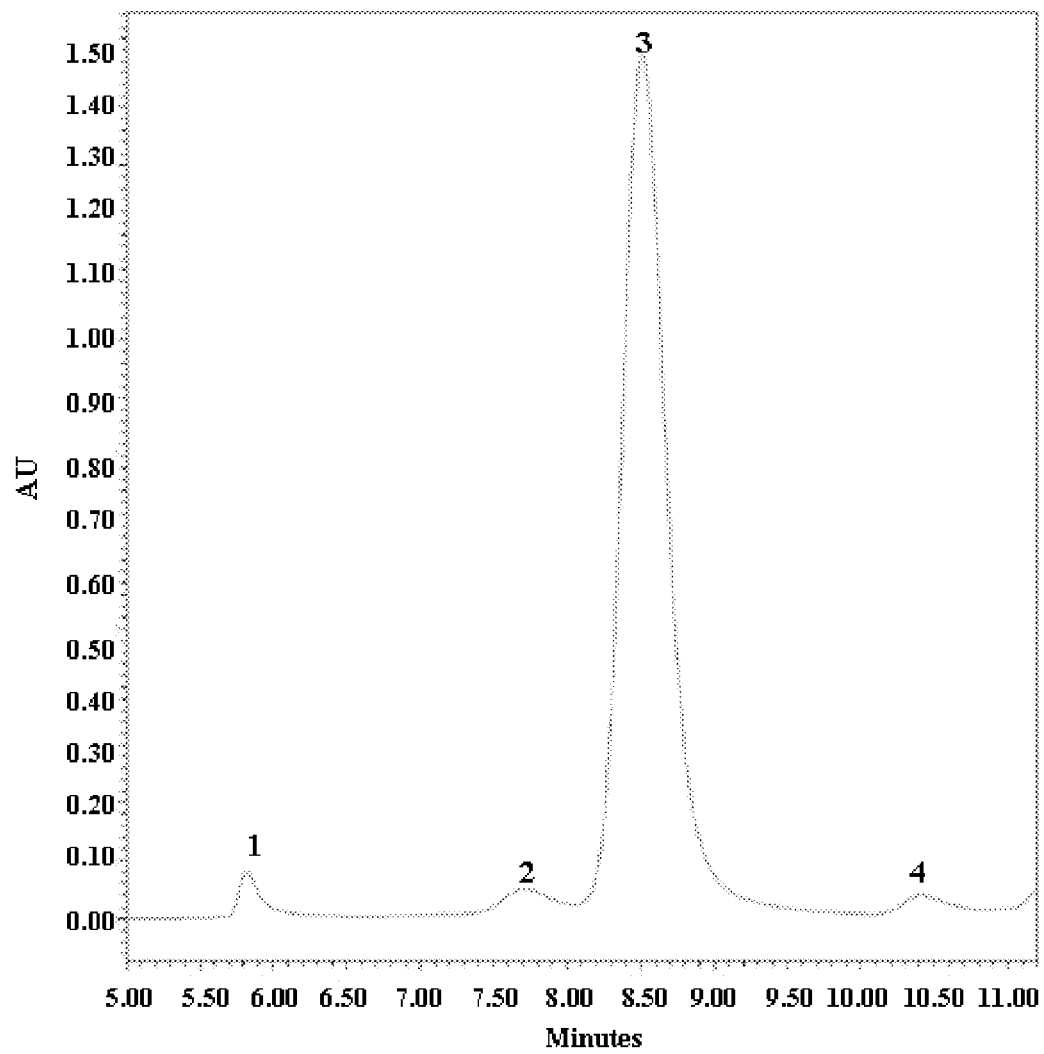

[Fig. 6]
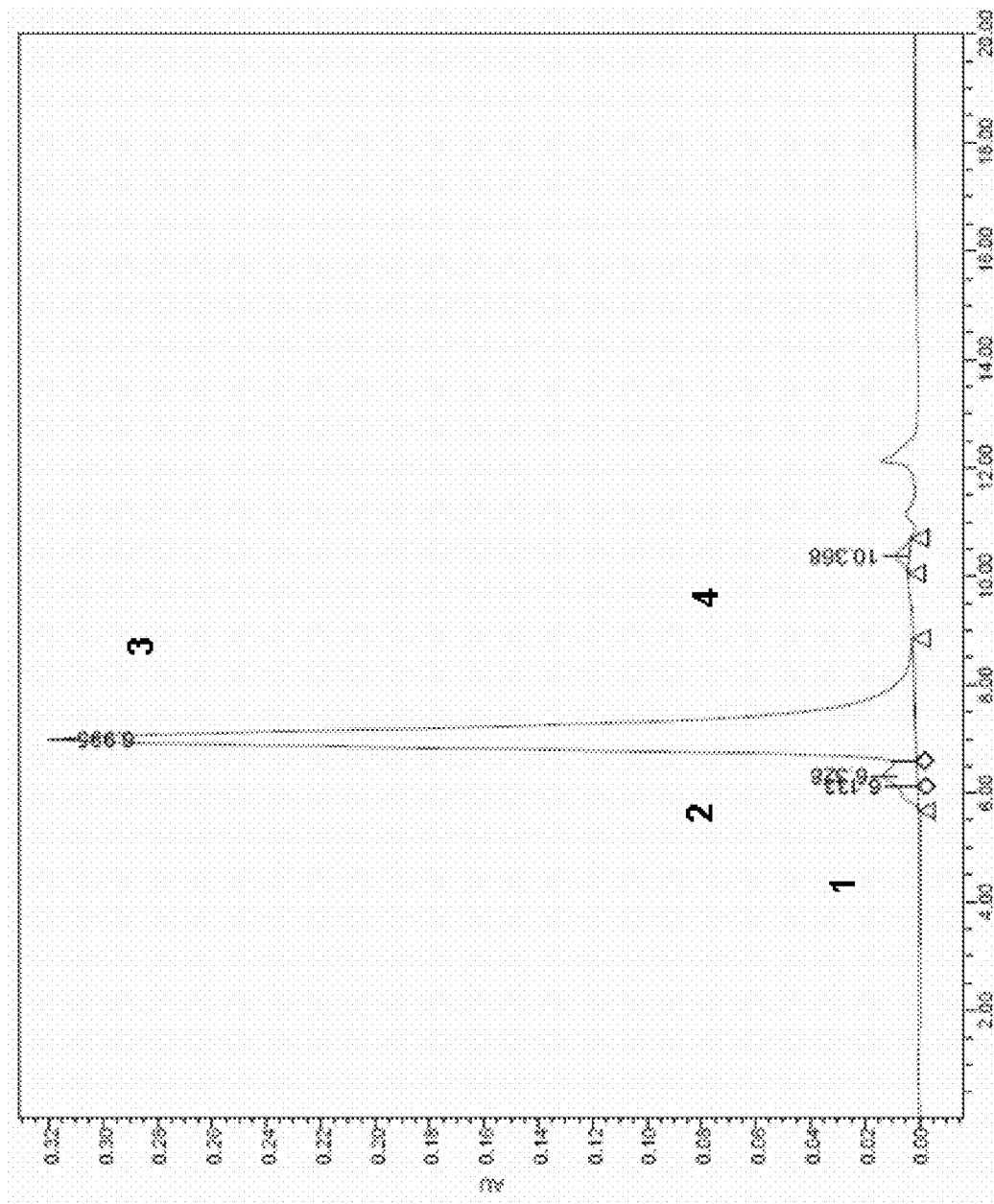

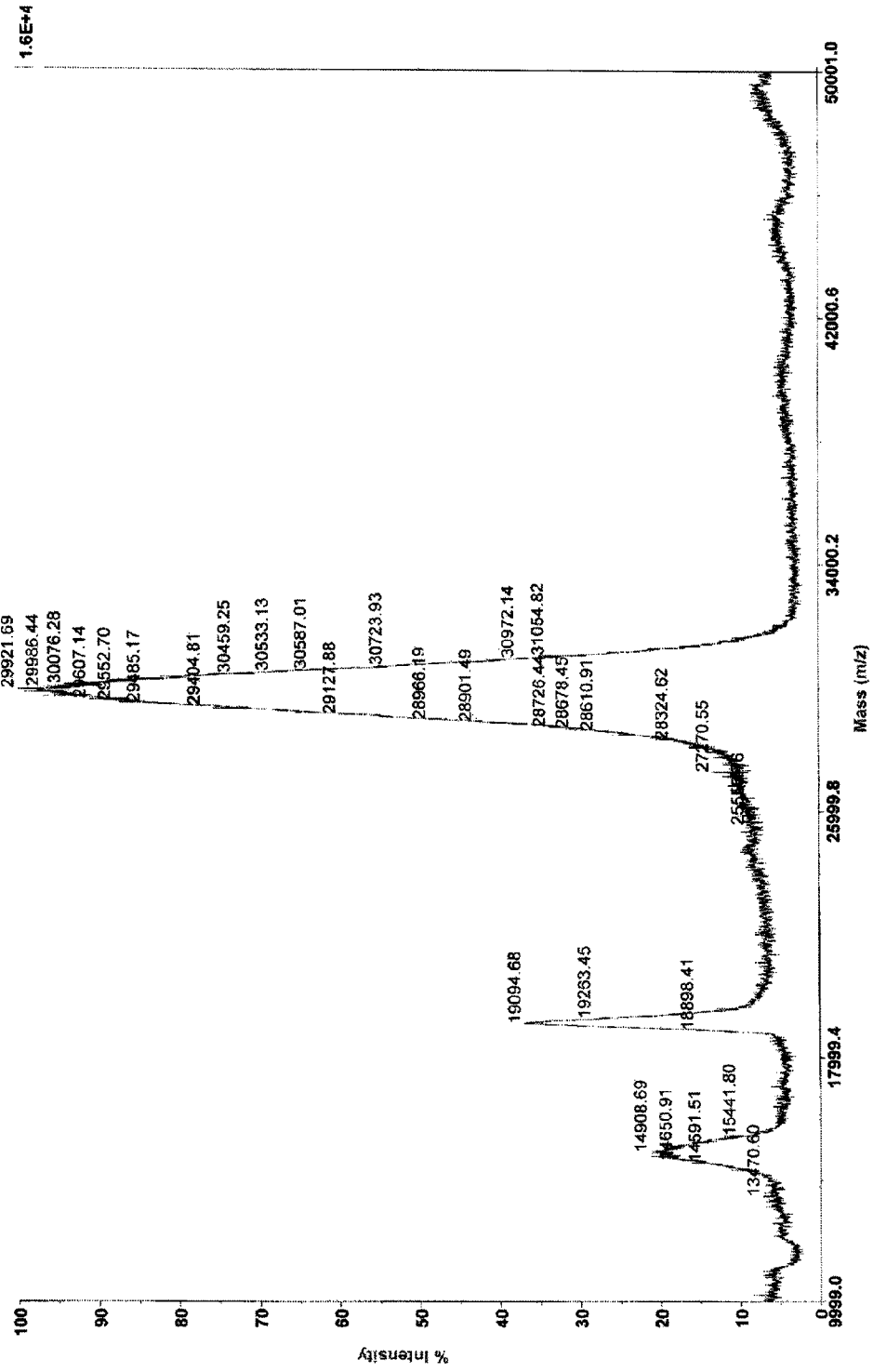
[Fig. 7]

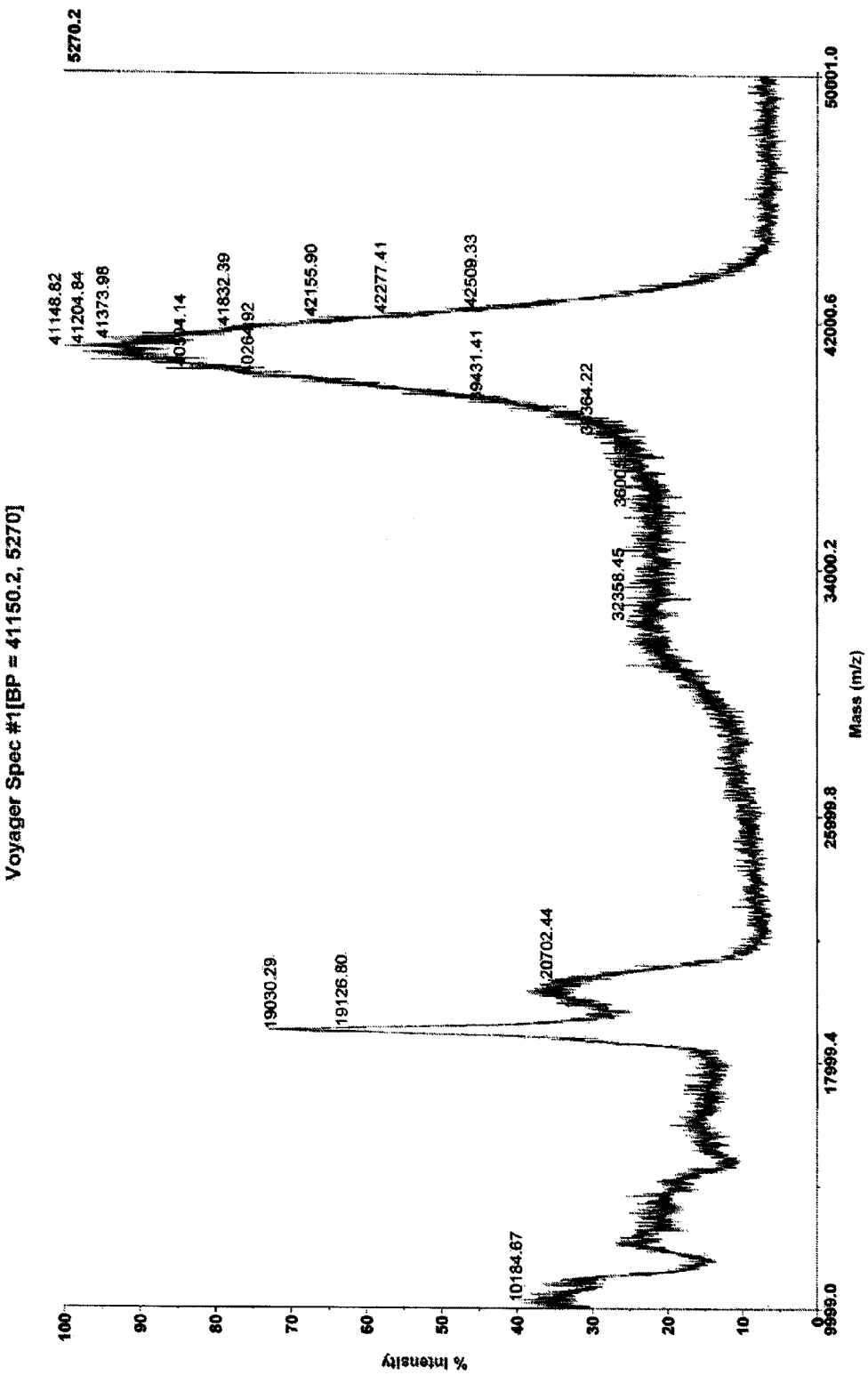
[Fig. 8]

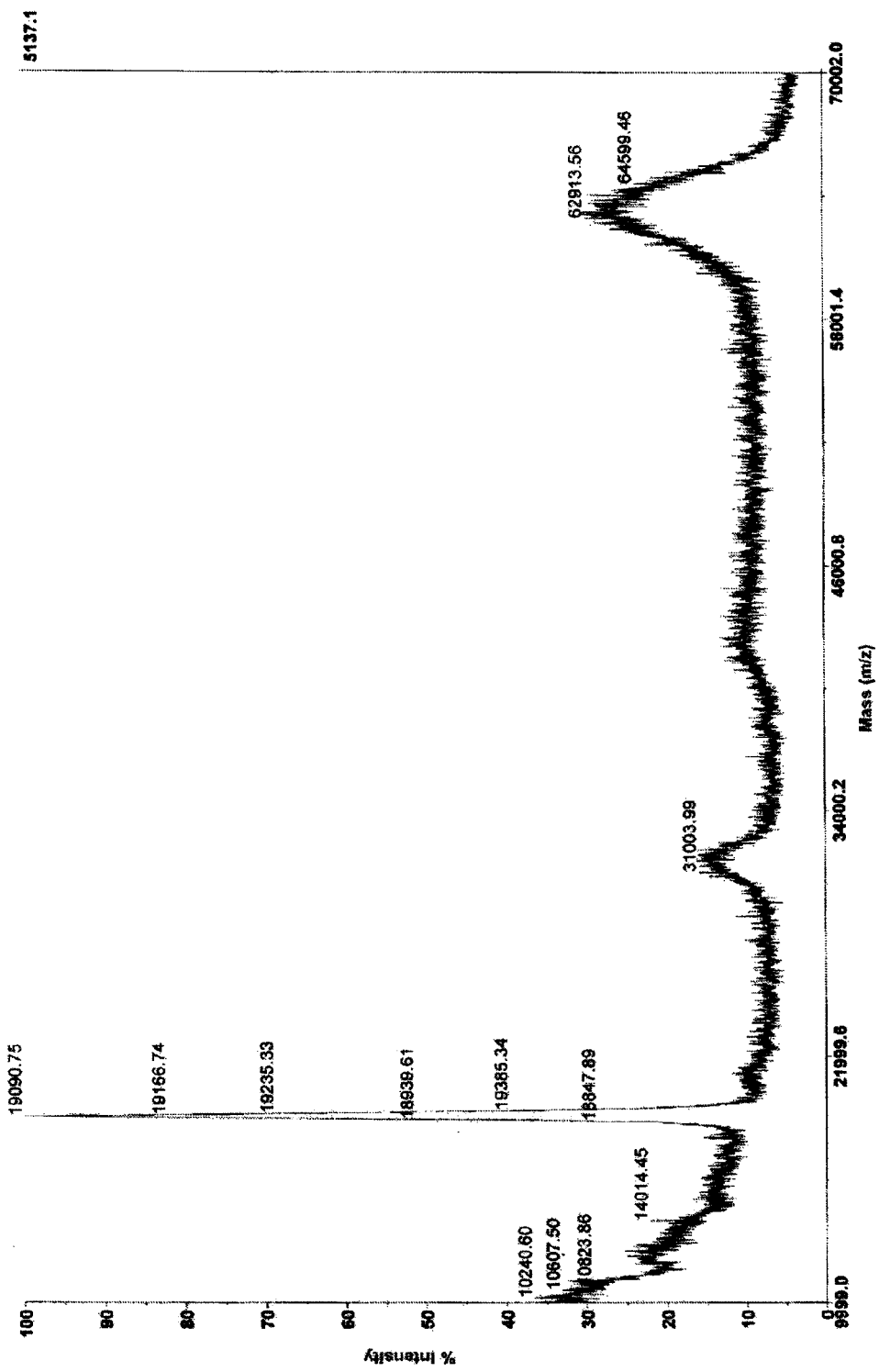
[Fig. 9]

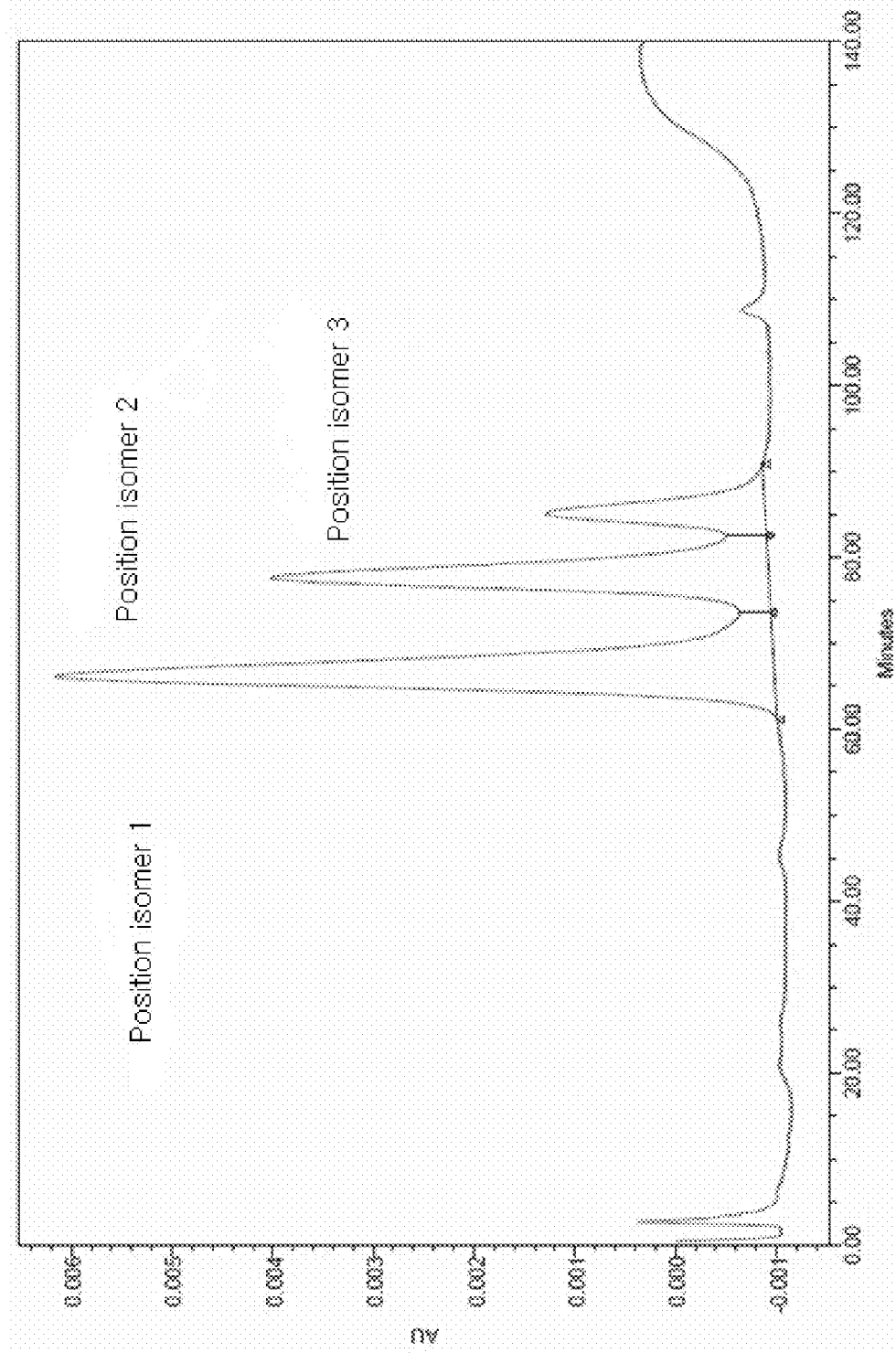

[Fig. 11]
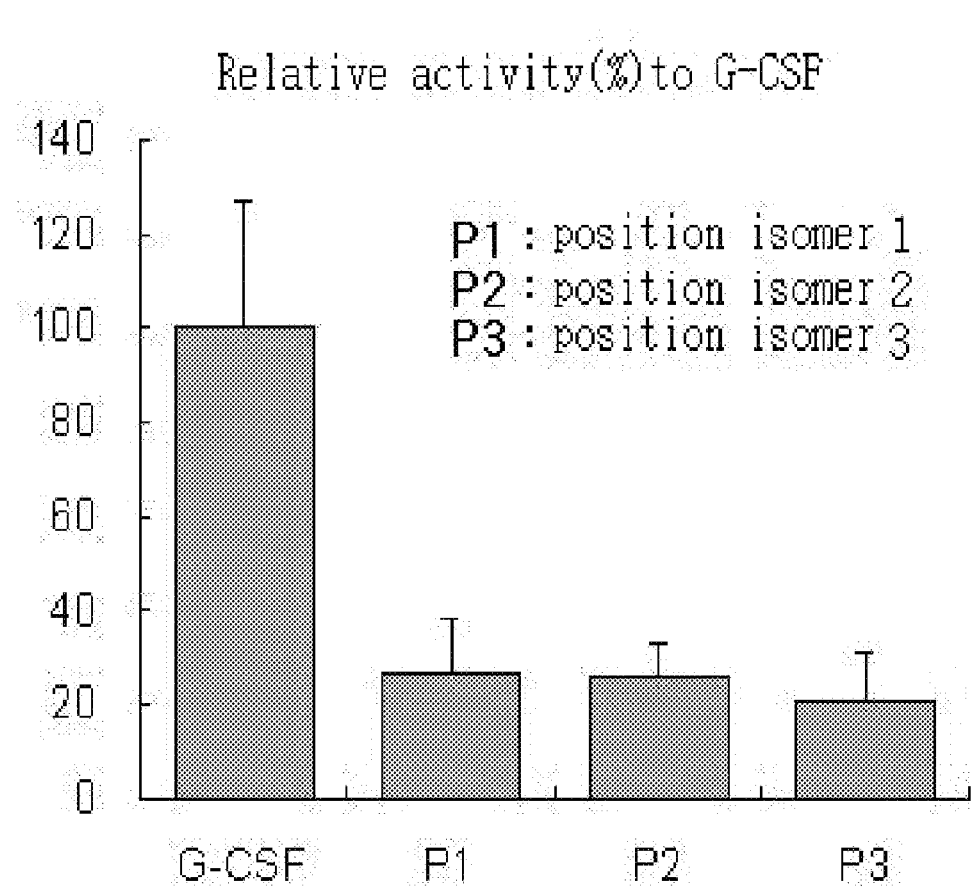

THREE-BRANCHED POLYETHYLENE GLYCOL-G-CSF CONJUGATE

CROSS REFERENCE TO RELATED APPLICATIONS

This application is a 35 U.S.C. §371 National Phase Entry Application from PCT/KR2006/004908, filed Nov. 22, 2006, and designating the United States, which claims priority under 35 U.S.C. §119 to Korean Patent Application No. 10-2006-0113721 filed Nov. 17, 2006, which is incorporated herein in its entirety.

TECHNICAL FIELD

The present invention relates to a three-branched PEG-G-CSF conjugate.

BACKGROUND ART

Colony stimulating factor (CSF), as a glycoprotein acting on production, division, and activity of hematopoietic cell, is classified into granulocyte colony stimulating factor (G-CSF), macrophage colony stimulating factor (M-CSF), granulocyte-macrophage colony stimulating factor (GM-CSF), multi colony stimulating factor (multi-CSF), etc.

It is known that G-CSF increases releasing of matured neutrophils into peripheral blood by facilitating production and division of neutrophilic precursor at bone marrow; induces a phagocytic activity by activating matured neutrophils; represents an antibody dependent cell mediated cytotoxicity; generates superoxides; and increases reactivity against chemotactic factor.

Human granulocyte colony stimulating factor (hG-CSF) was firstly separated from bladder carcinoma cell line 5637 by Welt et al. in 1985, and recombinant hG-CSF (rhG-CSF) was produced by cloning of gene from cDNA library of a cancer cell by Nagata et al., Souza et al. in 1986. rhG-CSF currently used in clinical trials is filgrastim binding methionine at N-terminal of protein without glycosylation, produced in *Escherichia coli*, and lenograstim with glycosylation, produced in animal cell.

In case of using rhG-CSF clinically, rhG-CSF has to be administrated once or more a day for decreasing leukocyte because rhG-CSF has a short duration of pharmacological effect. Thus, many studies have been conducted to increase a half-life of circulation of rhG-CSF using water-soluble polymer, thereby developing the drug to have a long duration of activity and high stability, and decreasing the frequency of administration.

And, polyethylene glycol in the water-soluble polymer is strongly hydrophilic, and can increase solubility at the time of bonding with protein for treatment. Also, polyethylene glycol is effective for increasing the molecular amount of protein bonded thereto, with maintaining main biological functions such as enzyme activity and receptor binding. Thus, polyethylene glycol can decrease the filtration of kidney, and effectively protect protein from proteolytic enzyme to decompose the protein. Therefore, many studies have been conducted to find out modifying methods of protein by using polyethylene glycol because it has the advantages to prevent protein decomposition, increase the stability and circulation time of protein, and decrease immunogenicity.

Korean Patent No. 0508358 disclosed conjugates and a preparing method thereof, wherein the conjugates have biological activities and are in the form of binding a biocompatibility polymer to thiol of cysteine residue of G-CSF, in the molar ratio of the polymer:G-CSF to stoichiometrically 0.7~1.3:1, preferably 1:1. But, since the cysteine residue of G-CSF which does not form disulfide bonds in G-CSF is main bonding part with G-CSF receptor, the conjugate using the cysteine residue has a drawback that its actual proliferation effect for neutrophil is little. And, because the conjugates immediately aggregate to bind a PEG to cysteine residues of G-CSF, it has a disadvantage that a small amount of SDS should be added to the conjugate to prevent the aggregation for safekeeping and the SDS was removed by ultrafiltration for administrating in vivo.

Korean Patent No. 0507796 disclosed PEG-homodimer conjugates binding a biological active polypeptide and a PEG, to increase the half-life in vivo of polypeptide. Particularly, it described that the homodimer binds an amino group of lycine residues of bioactive polypeptide of two molecules to a PEG to increase the residual time and sustain biological activities for a long time. But, the conjugates have less activity than mono-PEG conjugates because of conjugation of excessive PEGs and physicochemical and biological characteristics of the conjugates are not uniform because of non-specific conjugation.

And, the method of binding rhG-CSF to linear SCM-MPEG (Succinimidyl carboxymethyl ester of methoxy PEG) is known. The mono-PEG-G-CSF conjugates prepared by the method have 3 types of position isomers modified at N-terminal, lycine 35, and lycine 45 residues. Particularly, the conjugate modified at lycine 35 has a disadvantage leaving PEGs from the conjugate (Korean Patent No. 0248111, U.S. Pat. No. 5,824,784).

U.S. Pat. No. 5,951,974 disclosed conjugates of binding a linear SC-PEG (polyethylene glycol-N-succinimide carbonate) to gene recombination alpha interferon. The conjugates consist of covalent conjugates of urethane bond at $\epsilon$-amino group of lycine residues of interferon, $\alpha$-amino group of N-terminal cystaine residues, and an amino group of histidine residues. But, the conjugates have a disadvantage leaving PEGs from the conjugate because the urethane bond of conjugates are unstable.

Commonly used linear polyethylene glycol has a molecular weight of about 1,000~25,000 daltons, but has a limitation in binding many linear high molecules to protein or peptide, with maintaining their activities, due to limited biological active regions of protein and peptide.

Korean Patent No. 0254097 disclosed conjugates binding a two-branched PEG of a lycine skeletal structure to gene recombination alpha interferon. The conjugates have a merit to prevent PEG from binding to multi parts of interferon, and have 2 times the molecular weight of PEG by that of the linear PEG because two linear PEGs bind to a single part of interferon. But, the two-branched PEG can be hydrolyzed to a single chain for safekeeping or for reacting under an alkali condition because the two-branched PEG having a lycine skeletal structure has two urethane bonds in the PEG.

Generally, it is known that biological activity, durability, etc. of conjugates of binding a PEG to gene recombination protein is dependent on size and part modified in the PEG. But, it has not been known yet whether a size of PEG in conjugates binding PEG and rhG-CSF affects biological activities of a protein. Therefore, there has been a need in the art to overcome the disadvantages of the known method through controlling a size of PEG and binding to various skeletal structures of PEG not to decrease bioactivities of G-CSF and to increase the stability of binding parts.

DISCLOSURE OF THE INVENTION

Technical Problem

The object of the present invention is to provide three-branched polyethylene glycol (PEG)-G-CSF conjugates prepared by conjugating three-branched PEG and G-CSF, having high stability and same or more bioactivities of G-CSF than G-CSF and PEG-G-CSF conjugates known in the art; a preparation method of the same; and a pharmaceutical composition containing the same.

Technical Solution

To achieve the above object, the present invention provides three-branched polyethylene glycol (PEG)-G-CSF conjugates conjugated between three-branched PEG derivatives and G-CSF.

The present invention also provides a method of preparing three-branched PEG-G-CSF conjugates comprising conjugating three-branched PEG derivatives and G-CSF.

The present invention also provides a pharmaceutical composition comprising the conjugates.

The present invention also provides a method of treating neutropenia, preventing neutropenia, or facilitating increase of the number of neutrophil at the time of hematopoietic stem cell mobilization to peripheral blood and hematopoietic stem cell transplantation, comprising administrating the conjugate of the present invention as an effective ingredient.

The present invention is explained in detail below.

Three-branched PEG-G-CSF conjugates of the present invention may be prepared by conjugating three-branched polyethylene glycol (PEG), represented by the following general formula (1):

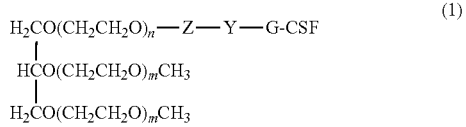

wherein,
n is an integer of 1 to 1,000;
m is an integer of 10 to 1,000;
Z is $(CH_2)_S$ or $(CH_2)_S NHCO(CH_2)_S$ as a linker of G-CSF and PEG wherein S is an integer of 1 to 6;
Y is an amide bond formed by combining $NH_2$ functional group in G-CSF and a functional group of PEG derivative.

The PEG has an average molecular weight of from 200 to 45,000 daltons, preferably from 20,000 to 45,000 daltons, more preferably from 23,000 to 43,000 daltons. Because a medicinally effective time can be changed according to an average molecular weight of PEG, the average molecular weight of PEG used in the present invention can be changed, depending on the time required for treatment.

The method of preparing three-branched PEG-G-CSF conjugate comprising conjugating three-branched PEG derivatives and G-CSF of the present invention is explained in detail below.

The three-branched PEG-G-CSF conjugates of general formula (1) are prepared by forming a covalent bond between three-branched PEG derivative of the following general formula (2) and G-CSF wherein PEG has an average molecular weight of from 200 to 45,000 daltons, preferably from 20,000 to 45,000 daltons, more preferably from 23,000 to 43,000 daltons:

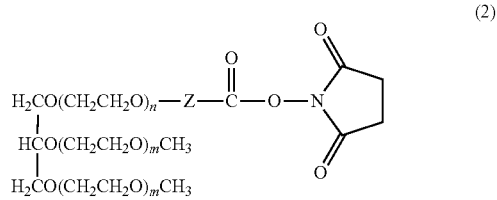

wherein,
n is an integer of 1 to 1,000;
m is an integer of 10 to 1,000;
Z is $(CH_2)_S$ or $(CH_2)_S NHCO(CH_2)_S$ as a linker of G-CSF and PEG wherein S is an integer of 1 to 6; and
the functional group which can chemically react with proteins and peptides containing G-CSF is N-hydrosuccinimide.

Three-branched PEG derivatives of the present invention activate high molecules having branched structure in which three linear biological receptive high molecules are combined. All of three OH (hydroxy) regions in the glycerol skeletal structure are polymerized with ethylene glycol unit molecules, and the end of one region is activated as a functional group. The other two regions except for the activated region are substituted with monomethoxy, to prevent additional reactions. When the above branched PEG derivatives are prepared, the size of each linear PEG can be controlled freely by a method known in the art.

Three-branched PEG derivatives in the present invention can be used as PEG derivatives, with the functional group chemically reacting with protein and peptide, known in the art. PEG derivatives of general formula (2) (with N-hydroxysuccinaimde) are preferable in terms of yield of the conjugate of the present invention.

The G-CSF in the present invention can be separated from mammalian organism or synthesized by a method known in the art such as gDNA cloning, cDNA cloning, etc. And, the G-CSF can be commercialized in the market.

And, the covalent bond between G-CSF and the three-branched PEG derivatives can be formed at a low temperature. The reaction is completed by adding acids, and the prepared three-branched PEG-G-CSF conjugates can be purified by a method known in the art such as the purification method using a cation exchange resin.

In the present invention, the reaction molar ratio of the G-CSF to the three-branched PEG derivative is from 1:0.5 to 1:50. A preferable molar ratio of the G-CSF to the three-branched PEG derivative is from 1:0.5 to 1:5 because the yield of mono PEG-G-CSF conjugate is decreased, as the molar ratio of polyethylene glycol to the G-CSF is increased.

The present invention also provides a pharmaceutical composition for treating or preventing symptoms caused by decreased hematopoietic function or decreased immunologic function. Particularly, clinical trials using the conjugate of the present invention as an effective showed that the number of neuctrophil was decreased, and the symptoms were relieved or controlled, for diseases caused in a treatment such as cancer chemotherapy or radiation therapy; infective diseases caused by bacteria, virus and fungus; other infective diseases; diseases caused by genetic or environmental reason such as severe chronic neutropenia and leukemia; or geriatric diseases caused by again. For example, symptoms caused by decreased hematopoietic function or decreased immunologic function are neutropenia caused by cancer chemotherapy for blood tumor or solid cancer, neutropenia caused by myelodysplastic syndrome, neutropenia caused by aplastic anemia, congenital idiopathic neutropenia, and neutropenia caused from treating human immunodeficiency virus.

The composition can be composed of PEG-G-CSF conjugates of the present invention or pharmaceutically acceptable diluent, antiseptics, solubilizer, emulsifier, adjuvant, and/or carrier.

The compositions of the present invention can be formulated to injection agent, capsule, tablet, liquid drug, pill, ointment, oculentum, collyrium, transdermal absorptive agent, paste, cataplasm, aerosols, etc.

And, the effective dosage of G-CSF is very small such as 0.1~500 μg (preferably, 5~50 μg). And, the drug comprising 0.1~500 μg of G-CSF may be administered to an adult, generally from 1 to 7 times a week. Thus, the effective dosage of the pharmaceutical composition of the present invention can be calculated by a known administration amount of G-CSF and a molecular weight of PEG used in the present invention. The effective dosage of pharmaceutical composition of the present invention may be varied, but generally once a week, and the composition can be administrated once or many times a day within a daily effective dosage range.

The following examples are intended to further illustrate the present invention, and the scope of the present invention is not intended to be limited thereby in any way.

Advantageous Effects

The three-branched PEG-G-CSF conjugates of the present invention are more pharmaceutically stable than linear- or two-branched PEG-G-CSF conjugates in the aspect of leaving PEGs from PEG-G-CSF conjugates and forming the aggregates of conjugates. And, the conjugates of the present invention can be used without additional separations of position isomers because the conjugates consist of position isomers with similar activities. And, the composition of the present invention has the effects of continuous production of neutrophilias and increased in-vivo half-life.

DESCRIPTION OF THE DRAWINGS

FIG. 1 is a schematic drawing illustrating the analytic results of a mixture formed to prepare conjugates of three-branched PEG having MW 23,000 Da and G-CSF according to Example 1, by size-exclusion high performance liquid chromatography.

FIG. 2 is a schematic drawing illustrating the analytic results of a mixture formed to prepare conjugates of three-branched PEG having MW 43,000 Da and G-CSF according to Example 2, by size-exclusion high performance liquid chromatography.

FIG. 3 is a schematic drawing illustrating the analytic results of a mixture formed to prepare conjugates of linear PEG having MW 10,000 Da and G-CSF according to Comparative Example 1, by size-exclusion high performance liquid chromatography.

FIG. 4 is a schematic drawing illustrating the analytic results of the purities of mono three-branched PEG-G-CSF conjugates separated from the mixture of Example 1, by size-exclusion high performance liquid chromatography.

FIG. 5 is a schematic drawing illustrating the analytic results of the purities of mono three-branched PEG-G-CSF conjugates separated from the mixture of Example 2, by size-exclusion high performance liquid chromatography.

FIG. 6 is a schematic drawing illustrating the analytic results of the purities of mono linear PEG-G-CSF conjugates separated from the mixture of Comparative Example 1, by size-exclusion high performance liquid chromatography.

FIG. 7 is a schematic drawing illustrating the analytic results of mono three-branched PEG-G-CSF conjugates separated from the mixture of Example 1, by Matrix-Assisted Laser Desorption Ionization (MALDI-TOF) Mass Spectrometry.

FIG. 8 is a schematic drawing illustrating the analytic results of mono three-branched PEG-G-CSF conjugates separated from the mixture of Example 2, by Matrix-Assisted Laser Desorption Ionization (MALDI-TOF) Mass Spectrometry.

FIG. 9 is a schematic drawing illustrating the analytic results of mono linear PEG-G-CSF conjugates separated from the mixture of Comparative Example 1, by Matrix-Assisted Laser Desorption Ionization (MALDI-TOF) Mass Spectrometry.

FIG. 10 is a schematic drawing illustrating the analytic results of the position isomers comprising mono three-branched PEG-G-CSF conjugates separated from the mixture of Example 1, by ion exchange chromatography.

FIG. 11 is a schematic drawing illustrating the analytic results of biological activity of the position isomers of mono three-branched PEG-G-CSF conjugates separated from the mixture of Example 1, according to Experimental Example 1, by the method of Experimental Example 2.

MODE FOR INVENTION

Example 1

Preparation of Three-Branched Polyethylene Glycol (PEG MW 23,000 Da)-G-CSF conjugates 10 mg of rhG-CSF (Dong-A Pharm. Co., Ltd.) was filtrated with pH8.5 and 50 mM of sodium borate buffer solution. Then 9.2 mg of three-branched PEG having N-hydroxysuccinimide (NOF corporation, Japan) and the molecular weight of 23,000 daltons was added to the solution in the molar ratio of rhG-CSF:three-branched PEG to 1:0.75. And, the solution was stirred at 4° C. for 90 min. The reaction was stopped by adding 100 mM of HCL to make the solution pH 4 and by diluting with sterile distilled water of 5 times the volume of the solution. Then, the mixture was inputted in SP-Sepharose Fast Flow cation exchange chromatography (Amersham Pharmacia Biotech) equalized with 20 mM of sodium acetate (pH4.0) buffer solution, and three-branched PEG-G-CSF conjugate was separated. The mixture was fractioned by using 0~1 M of concentration gradient of sodium chloride (NaCl). The molar ratio of three-branched PEG to G-CSF in the three-branched PEG-G-CSF conjugates was confirmed by HPLC and SDS-PAGE. And, di- or more (tri-, tetra- . . . ) three-branched PEG-G-CSF conjugates, unreacted G-CSF remaining after the reaction, etc. were excluded. And, the eluates were concentrated and sterilized-filtered to obtain the mono-three-branched PEG-G-CSF conjugate in which a G-CSF and a three-branched PEG (MW 23,000 Da) are conjugated (or called as mono-three-branched PEG-G-CSF conjugate).

It was confirmed that the reaction mixture consisted of 35.4% of mono-three-branched PEG-G-CSF conjugate (mono-PEG-G-CSF conjugate), about 59.4% of G-CSF unmodified by PEG, and the others [di-three-branched PEG-G-CSF conjugate (di-PEG-G-CSF conjugate), and N-hydroxysuccinimide (NHS)], by a size-exclusion high performance chromatography (see FIG. 1, wherein 1 and 2 represent di-PEG-G-CSF conjugate, 3 represents mono-PEG-G-CSF conjugate, 4 represents G-CSF unmodified by PEG, and 5 represents NHS leaving from three-branched PEG). And, the purity of mono-three-branched PEG-G-CSF separated from the mixture was measured by size-exclusion high performance liquid chromatography (see FIG. 4, wherein 2 represents di-PEG-G-CSF conjugate, and 3 represents mono-PEG-G-CSF conjugate) and the molecular weight was measured by matrix assisted laser desorption/ionization time-of-flight (MALDI-TOF) mass spectrometry (see, FIG. 7: the analytic result of mono-three-branched PEG-G-CSF by MALDI-TOF/MS). And, the position isomers were separated by cation exchange resin analytic column (SP-5WP, TOSOH) to confirm that the ratio for each position isomer is about 54%:33%:10% (see, FIG. 10). And, it was confirmed that each position isomer has very similar activity, in the experiment for biological activity of each position isomer (see, FIG. 11)

Example 2

Preparation of Three-Branched Polyethylene Glycol (PEG MW 43,000 Da)-G-CSF Conjugates 10 mg of rhG-CSF (Dong-A Pharm. Co., Ltd.) was filtrated with pH8.5 and 50 mM of sodium borate buffer solution. Then, 17.2 mg of three-branched PEG with N-hydroxysuccinimide (NOF corporation, Japan) and the molecular weight of 43,000 daltons was added to the solution to make the molar ratio of the rhG-CSF:the three-branched PEG to 1:0.75. And, the solution was stirred at 4° C. for 90 min. And, the reaction was stopped by adding 100 mM of HCl to make the solution pH 4 and by diluting with sterile distilled water of 5 times the solution volume. And, the mixture was inputted in SP-Sepharose Fast Flow cation exchange chromatography (Amersham Pharmacia Biotech) equalized with 20 mM of sodium acetate (pH4.0) buffer solution, and three-branched PEG-G-CSF conjugate was separated therefrom. The mixture was fractioned by using 0~1 M of concentration gradient of sodium chloride (NaCl). The molar ratio of three-branched PEG to G-CSF in the three-branched PEG-G-CSF conjugates was confirmed by HPLC and SDS-PAGE. And di- or more (tri, tetra . . . )-three-branched PEG-G-CSF conjugates, unreacted G-CSF remaining after the reaction, etc. were excluded. And, the eluates were concentrated and sterilized-filtered to obtain the mono-three-branched PEG-G-CSF conjugate in which a G-CSF and a three-branched PEG (MW 43,000 Da) are conjugated (or called as mono-three-branched PEG-G-CSF conjugate).

It was confirmed that the mixture of the reaction consisted of 18.7% of mono-three-branched PEG-G-CSF conjugate (mono-PEG-G-CSF conjugate), about 40.1% of G-CSF unmodified by PEG, and the others [di-three-branched PEG-G-CSF conjugate (di-PEG-G-CSF conjugate), and N-hydroxysuccinimide (NHS)] by size-exclusionhigh performance chromatography (see FIG. 2, wherein 2 represents di-PEG-G-CSF conjugate, 3 represents mono-PEG-G-CSF conjugate, and 4 represents G-CSF unmodified by PEG). And, the purity of mono-three-branched PEG-G-CSF separated from the mixture was measured by size-exclusion high performance liquid chromatography (see FIG. 5, wherein 1 represents oligo-PEG-G-CSF conjugate, 2 represents di-PEG-G-CSF conjugate, and 3 represents mono-PEG-G-CSF conjugate), and the molecular weight was measured by matrix assisted laser desorption/ionization time-of-flight (MALDI-TOF) mass spectrometry (see, FIG. 8; the analytic result of mono-three-branched PEG-G-CSF by MALDI-TOF/MS).

Comparative Example 1

Preparation of Linear Polyethylene Glycol (PEG MW 10,000 Da)-G-CSF Conjugates 10 mg of rhG-CSF (Dong-A Pharm. Co., Ltd.) was filtrated with pH8.5 and 50 mM of sodium borate buffer solution. And, 5.2 mg of linear PEG with N-hydroxysuccinimide (NOF corporation, Japan) and the molecular weight of 13,000 daltons was added to the solution to make the molar ratio of the rhG-CSF:the linear PEG to 1:0.75. And, the solution was stirred at 4° C. for 90 min. And, the reaction was stopped by adding 100 mM of HCL to make the solution pH 4 and by diluting with sterile distilled water of 5 times the solution volume. And, the mixture was inputted in SP-Sepharose Fast Flow cation exchange chromatography (Amersham Pharmacia Biotech) equalized with 20 mM of sodium acetate (pH4.0) buffer solution, and linear-branched PEG-G-CSF conjugate was separated therefrom. The mixture was fractioned by using 0~1 M of concentration gradient of sodium chloride (NaCl). The molar ratio of linear PEG to G-CSF in the linear PEG-G-CSF conjugate was confirmed by HPLC and SDS-PAGE. And, di- or more (tri, tetra . . . )-linear PEG-G-CSF conjugates, unreacted G-CSF remaining after the reaction, etc. were excluded. And, the eluates were concentrated and sterilized-filtered to obtain the mono-linear PEG-G-CSF conjugate in which a G-CSF and a linear PEG (MW 13,000 Da) are conjugated (or called as mono-linear PEG-G-CSF conjugate).

It was confirmed that the mixture of the reaction consisted of 45.6% of mono-linear PEG-G-CSF conjugate (mono-PEG-G-CSF conjugate), about 45.9% of G-CSF unmodified by PEG, and the others [di-linear PEG-G-CSF conjugate (di-PEG-G-CSF conjugate), and N-hydroxysuccinimide (NHS)], by a size-exclusion high performance chromatography (see FIG. 3, wherein 1 represents oligo-PEG-G-CSF conjugate, 2 represents di-PEG-G-CSF conjugate, 3 represents mono-PEG-G-CSF conjugate, and 4 represents G-CSF unmodified by PEG). And, the purity of mono-linear-branched PEG-G-CSF separated from the mixture was measured by size-exclusion high performance liquid chromatography (see FIG. 6, wherein 1 represents oligo-PEG-G-CSF conjugate, 2 represents di-PEG-G-CSF conjugate, 3 represents mono-PEG-G-CSF conjugate, and 4 represents G-CSF unmodified by PEG), and the molecular weight was measured by matrix assisted laser desorption/ionization time-of-flight (MALDI-TOF) mass spectrometry (see, FIG. 9).

Comparative Example 2

Preparation of Linear Polyethylene Glycol (PEG MW 20,000 Da)-G-CSF Conjugates 10 mg of rhG-CSF (Dong-A Pharm. Co., Ltd.) was filtrated with pH8.5 and 50 mM of sodium borate buffer solution, and then 8.0 mg of linear PEG having N-hydroxysuccinimide (NOF corporation, Japan) and the molecular weight of 20,000 daltons was added to the solution to make the molar ratio of the rhG-CSF:the linear PEG to 1:0.75. And, the solution was stirred at 4° C. for 90 min. The reaction was stopped by adding 100 mM of HCL to make the solution pH 4 and by diluting with sterile distilled water of 5 times the solution volume. Then, the mixture was inputted in SP-Sepharose Fast Flow cation exchange chromatography (Amersham Pharmacia Biotech) equalized with 20 mM of sodium acetate (pH4.0) buffer solution, and linear-branched PEG-G-CSF conjugate was separated therefrom. The mixture was fractioned by using 0~1 M of concentration gradient of sodium chloride (NaCl). The molar ratio of linear PEG to G-CSF in the linear PEG-G-CSF conjugate was confirmed by HPLC and SDS-PAGE. And, di- or more (tri, tetra . . . )-linear PEG-G-CSF conjugates, unreacted G-CSF remaining after the reaction, etc. were excluded. And, the eluates were concentrated and sterilized-filtered to obtain the mono-linear PEG-G-CSF conjugate in which a G-CSF and a a linear PEG (MW 20,000 Da are conjugated (or called as mono-linear PEG-G-CSF conjugate).

Comparative Example 3

Preparation of Two-Branched Polyethylene Glycol (PEG MW 20,000 Da, Lycine Skeletal Structure)-G-CSF Conjugates 10 mg of rhG-CSF (Dong-A Pharm. Co., Ltd.) was filtrated with pH8.5 and 50 mM of sodium borate buffer solution, and then 9.1 mg of two-branched PEG having N-hydroxysuccinimide (Nektar, USA) and the molecular weight of 20,000 daltons was added to the solution to make the molar ratio of the rhG-CSF:the linear PEG to 1:0.75. And, the solution was stirred at 4° C. for 90 min. The reaction was stopped by adding 100 mM of HCL to make the solution pH 4 and by diluting with sterile distilled water of 5 times the solution volume. Then, the mixture was inputted in SP-Sepharose Fast Flow cation exchange chromatography (Amersham Pharmacia Biotech) equalized with 20 mM of sodium acetate (pH4.0) buffer solution, and linear-branched PEG-G-CSF conjugate was separated therefrom. The mixture was fractioned by using 0~1 M of concentration gradient of sodium chloride (NaCl). The molar ratio of two-branched PEG to G-CSF in the two-branched PEG-G-CSF conjugate was confirmed by HPLC and SDS-PAGE. And, di- or more (tri, tetra . . . )-two branched PEG-G-CSF conjugates, unreacted G-CSF remaining after the reaction, etc. were excluded. And, the eluates were concentrated and sterilized-filtered to obtain the mono-two-branched PEG-G-CSF conjugate in which a G-CSF and a two-branched PEG (MW 20,000 Da are conjugated (or called as mono-linear PEG-G-CSF conjugate).

Comparative Example 4

Preparation of Two-Branched Polyethylene Glycol (PEG MW 20,000 Da, Glyerine Skeletal Structure)-G-CSF Conjugates 10 mg of rhG-CSF (Dong-A Pharm. Co., Ltd.) was filtrated with pH8.5 and 50 mM of sodium borate buffer solution. And, 8.0 mg of two-branched PEG having N-hydroxysuccinimide (NOF, Japan) and the molecular weight of 20,000 daltons was added to the solution to make the molar ratio of the rhG-CSF: the linear PEG to 1:0.75. The solution was stirred at 4° C. for 90 min. And, the reaction was stopped by adding 100 mM of HCL to make the solution pH 4 and by diluting with sterile distilled water of 5 times the solution volume. Then, the mixture was inputted in SP-Sepharose Fast Flow cation exchange chromatography (Amersham Pharmacia Biotech) equalized with 20 mM of sodium acetate (pH4.0) buffer solution, and linear-branched PEG-G-CSF conjugate was separated therefrom. The mixture was fractioned by using 0~1 M of concentration gradient of sodium chloride (NaCl). The molar ratio of two-branched PEG to G-CSF in the two-branched PEG-G-CSF conjugate was confirmed by HPLC and SDS-PAGE. And, di- or more (tri, tetra . . . )-two branched PEG-G-CSF conjugates, unreacted G-CSF remaining after the reaction, etc. were excluded. And, the eluates were concentrated and sterilized-filtered to obtain the mono-two-branched PEG-G-CSF conjugate in which a G-CSF and a two-branched PEG (MW 20,000 Da) are conjugated (or called as mono-linear PEG-G-CSF conjugate).

Comparative Example 5

Preparation of Mono-Methoxypolyethylene Glycol-G-CSF Conjugates Binding at N-Terminal α-Amino Residue The title conjugate was prepared by a method described in Korean Patent No. 0248111, and U.S. Pat. No. 5,824,784. The method as briefly described is as follows.

100 mM of sodium phosphate containing 20 mM of NaCNBH$_3$, and 5 mg/ml of rhG-CSF were stirred at 4° C. And, 5 times mol of linear methoxylpolyethylene glycol (mPEG) aldehyde (Nektar, USA) was added to the solution, which was stirred for 10 hs. The reaction was stopped by adding 100 mM of HCL to make the solution pH 4 and by diluting with sterile distilled water of 5 times the solution volume. Then, the mixture was inputted in SP-Sepharose Fast Flow cation exchange chromatography (Amersham Pharmacia Biotech) equalized with 20 mM of sodium acetate (pH4.0) buffer solution, and linear-branched PEG-G-CSF conjugate was separated therefrom. The mixture was fractioned by using 0~1 M of concentration gradient of sodium chloride (NaCl). And, the eluates were concentrated and sterilized-filtered to obtain the mono-mPEG-G-CSF conjugate in which a G-CSF and a two-branched PEG (MW 20,000 Da) are conjugated (or called as mono-linear PEG-G-CSF conjugate).

Comparative Example 6

Preparation of Mono-Methoxypolyethylene Glycol-G-CSF Conjugates Binding at Thiol Group of Cysteine Residue of G-CSF The title conjugate was prepared by a method described in Korean Patent No. 0508358. The method as briefly described is as follows.

1 mg of rhG-CSF (Dong-A Pharm. Co., Ltd.) was added to 1 mL of sodium phosphate buffer solution (0.1 M) having pH8.5, and 52.6 mg of polyethylene glycol maleimide (NOF, Japan) was added to the solution. And, the solution was stirred for 1 h at room temperature. Then, PEG derivatives remaining after the reaction were removed from the solution by centricon 30 (Amicon, USA). And, the solution was concentrated and sterilized-filtered to obtain the mono-mPEG-G-CSF conjugate.

The property and pharmacological activity tests were conducted by using the conjugates prepared above, and the results are as follows.

Experimental Example 1

Analytic Separation of Position Isomers of Three-Branched PEG-G-CSF Conjugates

100 μg of Mono-three-branched PEG-G-CSF conjugates of Example 1 was input to a cation exchange resin analytic column (SP-5WP, TOSOH) equalized with 25 mM of sodium acetate buffer (pH 4.0, controlled with glacial acetic acid), and each position isomer of the conjugates was separated by 100 mM of sodium acetate buffer, pH 7.8). It was confirmed that the ratio of each position isomer is about 54%:33%:10% (see, FIG. 10).

Experimental Example 2

Analysis of Biological Activities of Position Isomers of Three-Branched PEG-G-CSF Conjugates Relative Biological activities of position isomers of three-branched PEG-G-CSF conjugates of Example 1 were measured by using that of G-CSF.

NFS-60 cell strain cultured at growth RPMI 1640 containing 10% FBS and 1 ng/ml of rmIL-3 was washed 3 times with test RPMI 1640 containing 5% FBS. And, the cell strain was divided into 100 ml ($2 \times 10^5$ cells/ml) at 96 well plate. Then the sample was diluted with test medium to prepare a sample of 200 ng/ml, and 9 more samples of 200 ng/ml by 5 times gradient, and the samples were divided into 3 wells, each 100 ml, per concentration in 96 well plates containing the cell solutions.

Each well was cultured at 37° C. and 5% $CO_2$ incubator for 48 hs, 40 µl of MTS was added to each well. After 2 hs, an absorbance of the sample was measured at 490 nm by an ELISA reader. $EC_{50}$ was calculated by a dose response curve and a linear regression analysis of point comprised straight line of a standard curve, and the activities of position isomers were determined (see, FIG. 11). The three-branched PEG-G-CSF conjugates of the present invention have position isomers having similar activities. That is, it is not necessary to remove some position isomers having relatively lower activity because the three-branched PEG-G-CSF conjugates of the present invention are composed of conjugates with uniformed activities Experimental Example 3

Pharmacokinetics Test of the Three-Branched PEG-G-CSF Conjugates

The pharmacodynamic test was conducted to inject hypodermically each of G-CSF, the PEG-G-CSF conjugates of Example 1, and the PEG-G-CSF conjugates of Example 2, into test rats (Sprague Dawley) which had 240~260 g of body weights. After injecting them in the amount of 400 µg per rat, the blood samples were collected from the rats at 0 min, 30 min, 1 hr, 2 hr, 3 hr, 4 hr, 8 hr, 12 hr, 1 day, 2 days, 3 days, 4 days, 5 days, 6 days, and 7 days, after the injection. And, the concentrations of the G-CSF conjugates in the sample were quantitatively analyzed by an enzyme-linked immunosorbent assay (ELISA) kit (Biosource, USA).

The half-life in blood of the PEG-G-CSF conjugates of Example 1 and Example 2 was increased 3 times and 10.8, respectively, compared with that of G-CSF, and the areas under the concentration time curve in blood of the conjugates of Example 1 and Example 2 were also increased by 7.6 times and 23.4 times, respectively, compared with that of G-CSF [Table 1: Pharmacokinetics test of the three-branched PEG-G-CSF conjugates and G-CSF at rat (Sprague Dawley rat)]. It was confirmed by this test that pharmacokinetics of PEG-G-CSF conjugate is dependent on a size of PEG.

TABLE 1

|  | rhG-CSF | Example 1 | Example 2 |
|---|---|---|---|
| Cmax (hr) | 1383.2 | 1676.8 | 1710.6 |
| Tmax (hr) | 1.5 | 12 | 36 |
| $T_{1/2}$ (hr) | 2.9 | 8.7 | 31.2 |
| AUC (ng * hr/ml) | 6246.9 | 47420.3 | 146196.1 |

*The abbreviations in the above table have the following meanings:
Tmax: time to reach maximum concentration
Cmax: maximum concentration
$t_{1/2}$: elimination half-life
AUC: area under the concentration time curve.

Experimental Example 4

Stability Test of the Three-Branched PEG-G-CSF Conjugates on Leaving Pegs from the Conjugates PEG-G-CSF conjugates of Examples 1 and 2, and Comparative Examples 2, 3, and 4 were deposited under pH 7 and 37° C. for 7 days, and the aspects of leaving PEGs in length of time were analyzed by reversed-phase high-performance liquid chromatography, to estimate the degrees of leaving PEGs on a skeletal structure, molecular weights, and branched types of PEG.

In the PEG's skeletal structure, the leaving PEGs occurred most frequently in Comparative Example 2 using linear PEG. However, the leavings PEGs from the conjugates of Examples 1 and 2, and Comparative Example 4 occurred less frequently than those of Comparative Examples 2 and 3 (Table 2: Comparison of generation rates of G-CSF in PEG-G-CSF conjugates having various PEG skeletal structures). This test confirmed that the three-branched PEG-G-CSF conjugate is more stable than the linear-, two-branched PEG-G-CSF conjugates, and the conjugate with a glycerol skeletal structure is more stable than the conjugates with a lycine skeletal structure.

TABLE 2

|  | Example 1 | Example 2 | Comparative Example 2 | Comparative Example 3 | Comparative Example 4 |
|---|---|---|---|---|---|
| Δ(generation rate, %/day) | 0.44 | 0.34 | 5.59 | 1.36 | 0.54 |

Experimental Example 5

Stability Test to the Three-Branched PEG-G-CSF Conjugates Against Forming Aggregations According to a Skeletal Structure of Peg and a Type of Binding PEG to G-CSF Mono three-branched PEG-G-CSF conjugate of Example 1; mono PEG-G-CSF conjugate of Comparative Examples 2 and 4, having a similar molecular weight to the conjugate of Example 1 and different skeletal structure from the conjugate of Example 1; and mono PEG-G-CSF conjugate of Comparative Example 5 having different binding type from the conjugate of Example 1 were tested to measure stabilities against forming aggregations. Each sample was collected by 500 µl, and the solvent of the samples were exchanged 3 times with 100 mM of phosphate buffer solution having pH7. And, the samples were deposited at 37° C. for 14 days, and formation of aggregation of the conjugates was analyzed by size-exclusion high performance liquid chromatography.

The analysis results of forming of the aggregation represent that mono-PEG-G-CSF conjugate of Example 1 had most stability in the aspect of leaving PEGs, and formed the least aggregation (Table 3: Generation rates of aggregation conjugates according to a skeletal structure of PEG and a type of binding PEG to G-CSF). Mono-PEG-G-CSF conjugates of Comparative Examples 2 and 4 using PEG having the same glycerol skeletal structure as PEGs in Example 1, and using the same binding type to Example 1, as well as the conjugate of Example 1, formed some aggregation. However, mono-PEG-G-CSF conjugates of Comparative Example 3 using PEG having different skeletal structure from PEGs in Example 1 (although using the same binding type as Example 1) formed much aggregation. And, mono-PEG-G-CSF conjugates of Comparative Example 5 using PEG having different skeletal structure from PEGs in Example 1 and using the different binding type from Example 1 formed 2 times or more of aggregation, compared with the conjugates of Example 1.

TABLE 3

| sample | Example 1 | Comparative Example 2 | Comparative Example 3 | Comparative Example 4 | Comparative Example 5 |
|---|---|---|---|---|---|
| Generation rate (%) | 6.81 | 7.89 | 50.5 | 7.91 | 15.3 |

In conclusion, mono-three-branched PEG-G-CSF conjugate of Example 1 is most stable in both leaving PEGs from the conjugates and forming aggregation. That is, this advantageous effect is from different skeletal structures between branched PEG and branched PEG used in the present invention.

Experimental Example 6

Neutrophil Proliferation Activities Assay of PEG-G-CSF Conjugates at Animal Model to which an Anti-Cancer Medicine is Administrated Neutrophil proliferation activities of mono-three-branched PEG-G-CSF conjugates of Example 1, mono-mPEG (methoxy polyethylene glycol)-G-CSF conjugates of Comparative Examples 5 and 6 having different binding type and different molecular weight from the conjugates of Example 2 were assayed by mouse model to which an anti-cancer agent was administrated.

Mice (BDF1) of 20~25 g were administrated with 200 mg/kg of an anti-cancer agent (cyclophosphamide) to decrease the number of neutrophil for 2 days. And, each of the conjugate of Example 1 and the conjugates of Comparative Examples 5 and 6 was administrated subcutaneously once, 1 mg/kg per mouse, and G-CSF was administrated 8 times by 0.125 mg/kg per mouse to make the total administration amount 1 mg/kg. The mice' bloods were collected at 0, 1, 2, 3, 4, 5, 6, 7, 8, 9, 10 and 12 days, and the total numbers of leukocyte and neutrophil were measured by automatic hemocyte measuring instrument (HEMAVET 850, Drew Scientific Ltd., UK). The periods that started the recovery of neutrophils decreased by an anti-cancer agent and the times required for the recovery of neutrophil, in the conjugate of Example 1 and the conjugates of Comparative Examples 5 and 6 were similar. However, the time reaching the maximum number of neutrophil in the conjugate of Example 1 was about 12 hs faster than those of the conjugates of Comparative Examples 5 and 6. The area under the increased neutrophil count-time curve (AU-NC) of the conjugate of Example 1 was largest (Table 4: Neutrophil proliferation activities assay of PEG-G-CSF conjugates at animal model to which an anti-cancer medicine is administrated). Therefore, it was confirmed that mono-three-branched PEG-G-CSF conjugate has a rapid effect of Neutrophil proliferation.

TABLE 4

|  | G-CSF | Example 1 | Comparative Example 5 | Comparative Example 6 |
|---|---|---|---|---|
| Increase of neutrophil† | 2 days | 2 days | 2 days | 2 days |
| Recovery time of neutrophil* | 4.5 days | 4.5 days | 4.5 days | 4.5 days |
| neutrophil peak | 6 days | 5.5 days | 6 days | 6 days |
| AU-NC ($\times 10^9$ cells · day/L) | 24.4 | 54.0 | 52.1 | 34.6 |

†Time for neutrophil to be increased after administration of a medicine
*Time to reach 1,000/mm³ or more of neutrophil after administration of an anti-cancer medicine.

INDUSTRIAL APPLICABILITY

The three-branched PEG-G-CSF conjugates of the present invention are more pharmaceutically stable than linear- or two-branched PEG-G-CSF conjugates in terms of leaving PEGs from PEG-G-CSF conjugates and forming the aggregates of conjugates. And, the conjugates of the present invention can be used without additional separations of position isomers because the conjugates consist of the position isomers with similar activities. And, the composition of the present invention has the effects of continuous production of neutrophilias and increased in vivo half-life.

What is claimed is:

1. A three-branched PEG-G-CSF conjugate of the following general formula (1):

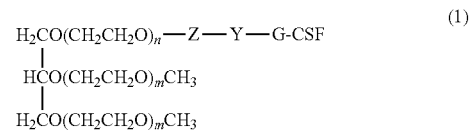

in which a bonding ratio of three-branched polyethylene glycol(PEG) and G-CSF is 1:1 (mol/mol), and PEG has an average molecular weight of about 23,000 daltons, wherein,
n is an integer of 1 to 1,000;
m is an integer of 10 to 1,000;
Z is $(CH_2)_s$ or $(CH_2)_s NHCO(CH_2)_s$ as a linker of G-CSF and PEG wherein S is an integer of 1 to 6;
Y is an amide bond formed by combining $NH_2$ functional group in G-CSF and a functional group of PEG derivative.

2. A method of preparing a three-branched PEG-G-CSF conjugate of the general formula (1) of claim 1 comprising:
preparing a mixed solution including a three-branched PEG derivative of the following general formula (2) and G-CSF;
reacting the three-branched PEG derivative and G-CSF by stirring the mixed solution at a temperature of about 4° C. for about 90 minutes to form a covalent bond between the three-branched PEG derivative of the following general formula (2) and G-CSF;

then adding an acid to the mixed solution to complete the reaction of the three-branched PEG derivative and G-CSF; and then identifying the three-branched PEG-G-CSF conjugate by subjecting said mixed solution to chromatography, wherein PEG (polyethylene glycol) has an average molecular weight about 23,000 daltons;

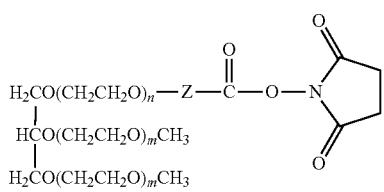

(2)

wherein, n is an integer of 1 to 1,000;

m is an integer of 10 to 1,000;

Z is $(CH_2)_s$ or $(CH_2)_sNHCO(CH_2)_s$ as a linker of G-CSF and PEG wherein S is an integer of 1 to 6; and the functional group which can chemically react with proteins and peptides containing G-CSF is N-hydroxysuccinimide.

3. The method of claim 2, wherein the molar ratio of G-CSF to three-branched PEG derivative is from 1:0.5 to 1:50.

4. The method of claim 3, wherein the molar ratio of G-CSF to three branched PEG derivative in the reaction is from 1:0.5 to 1:5.

5. A pharmaceutical composition comprising a three-branched PEG-G-CSF conjugate of the following general formula (1):

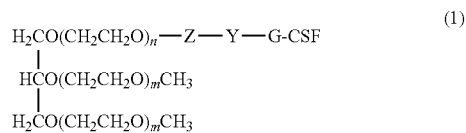

(1)

in which a bonding ratio of three-branched polyethylene glycol (PEG) and G-CSF is 1:1 (mol:mol), and PEG has an average molecular weight of 23,000 daltons, wherein, n is an integer of 1 to 1,000;

m is an integer of 10 to 1,000;

Z is $(CH_2)_S$ or $(CH_2)_S$ as a linker of G-CSF and PEG wherein S is an integer of 1 to 6;

Y is an amide bond formed b combining $NH_2$ functional group in G-CSF and a functional group of PEG derivative, and at least one pharmaceutically acceptable diluent, antiseptic, solubilizer, emulsifier, adjuvant, or combination thereof.

6. A method of treating neutropenia caused by treatment by cyclophosphamide in a patient in need thereof, comprising administering to said patient pharmaceutical composition of claim 5.

7. A composition comprising the three-branched PEG-G-CSF conjugate of claim 1, in further combination with at least one diluent, antiseptic, solubilizer, emulsifier, adjuvant, or combination thereof.

8. A composition comprising the conjugate of claim 1 as effective ingredient and at least one diluent, antiseptic, solubilizer, emulsifier, adjuvant, or combination thereof.

* * * * *